United States Patent [19]

Morandi et al.

[11] Patent Number: 5,779,905
[45] Date of Patent: Jul. 14, 1998

[54] PROCESS FOR THE DEPYROGENATION OF INJECTABLE PHARMACEUTICAL SOLUTIONS

[75] Inventors: Ervino Morandi; Angelo Gallotti, both of Milan, Italy

[73] Assignee: Dibra S.p.A., Milan, Italy

[21] Appl. No.: 453,342

[22] Filed: May 30, 1995

[51] Int. Cl.[6] .................................................. B01D 61/00
[52] U.S. Cl. .................... 210/651; 210/641; 210/195.2; 210/257.2; 210/650
[58] Field of Search ................................ 210/650, 651, 210/653, 195.2, 257.2, 900, 908, 652, 500.29, 654, 641; 424/9

[56] References Cited

U.S. PATENT DOCUMENTS

| | | | |
|---|---|---|---|
| 4,495,067 | 1/1985 | Klein et al. | 210/900 |
| 4,959,237 | 9/1990 | Walker | 210/652 |
| 5,073,268 | 12/1991 | Saito et al. | 210/651 |
| 5,104,546 | 4/1992 | Filson et al. | 210/651 |
| 5,160,437 | 11/1992 | Bosworth et al. | 210/651 |
| 5,171,767 | 12/1992 | Buckley et al. | 210/651 |
| 5,219,554 | 6/1993 | Groman et al. | 424/9 |
| 5,221,485 | 6/1993 | Bosworth et al. | 210/651 |
| 5,385,664 | 1/1995 | Oinuma et al. | 210/900 |
| 5,401,499 | 3/1995 | Hirayama et al. | 210/651 |

FOREIGN PATENT DOCUMENTS 0312104  4/1989  European Pat. Off. ........... 210/651

*Primary Examiner*—Ana Fortuna
*Attorney, Agent, or Firm*—Bucknam and Archer

[57] ABSTRACT

The present invention relates to a process for the preparation of injectable solutions of pharmaceutical products and/or of diagnostic agents, characterized by an extremely high degree of purity as regards the low content of bacterial endotoxins. The process of the invention provides for the prefiltering of the solutions by means of a microfiltering unit, a subsequent ultrafiltration and the recycling of the retentate from the ultrafiltration to the solution which emerges from the prefilter.

5 Claims, 2 Drawing Sheets

PROCESS FOR THE DEPYROGENATION OF INJECTABLE PHARMACEUTICAL SOLUTIONS

The present invention relates to the preparation of injectable solutions of pharmaceutical products and/or of diagnostic agents, characterized by an extremely high degree of purity as regards the low content of bacterial endotoxins.

It is known that injectable formulations of pharmaceutical products or of diagnostic agents must satisfy stringent criteria of sterility and of apyrogenicity, in order to be able to be administered to patients with acceptable margins of safety. Accordingly it is of fundamental importance to eliminate as completely as possible every pathogen and also the bacterial endotoxins, from the final formulation of the active principle before packaging, in order to avoid undesired and frequently hazardous reactions of the body to said toxic agents.

This requirement is all the more perceived in the preparation of diagnostic contrastographic formulations, where there is frequently the need of administering to the patient large volumes of highly concentrated solutions of said formulations.

Among the various diagnostic imaging techniques (X-ray, NMR, echography), it is worth mentioning, by way of example, the X-ray technique in which the opacifying contrastographic agent is preferably represented by a non-ionic iodine-containing aromatic compound.

To provide a sufficient contrast, the injectable solutions of these compounds are usually very concentrated, reaching approximately the value of 80% w/v, and, for example by the intravenous route, are administered in volumes which may reach 250 mL and above per single dose.

Another administration route adopted for these compounds is, for example, the intrathecal route for tests which concern the neural tissue and in this connection it is well known that this type of tissue proves to be very much more sensitive than the others to the toxic agents (up to 1000 times more sensitive).

It is accordingly clear that, especially in injectable solutions of these compounds, the presence of bacterial endotoxins must be as low as possible.

Figure 1:
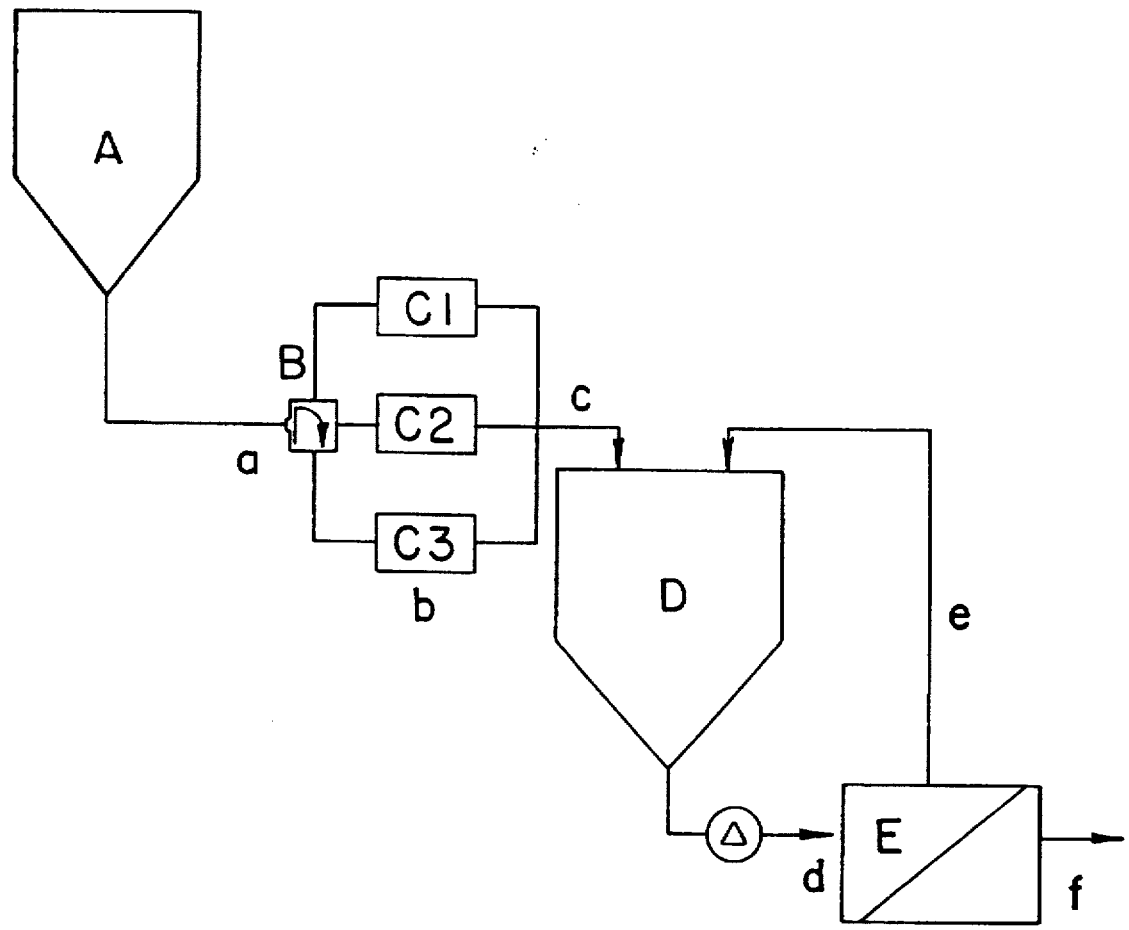
FIG. 1 illustrates a process used in the prior art for the depyrogenation of an injectable pharmaceutical solution.

Among those techniques for the depyrogenation of liquids which are in common use industrially, the use of microporous filters and of ultrafiltration membranes has by now become widespread.

Such membranes are, at all events, widely used, with particularly satisfactory results, for the treatment of water or of dilute solutions.

Unfortunately, the situation proves to be very different when it is desired to subject to ultrafiltration solutions of contrast media, such as in particular non-ionic iodine-containing compounds, which are very concentrated and viscous.

The problem is that by reason of the characteristics of these solutions, there is a need for filtering surfaces which are very large, in order to remain within the range of practicable production times which are industrially acceptable. By contrast, smaller surfaces would excessively extend the filtration times.

Consequently, the plant required is bulky and characterized by significant dead volumes in which non-negligible quantities of unfiltered solution stagnate, which solution, at the end of each working cycle, has to be discarded or recovered and treated separately in a suitable smaller plant. All this has significant unfavourable effects on the total production costs and, potentially, also on the final quality of the product.

An obvious attempt at resolving this difficulty consisted of the use of spiral-wound membranes for tangential ultrafiltration (having a suitable porosity capable of blocking the passage of the bacterial endotoxins: for example, an average cut-off of 10,000 dalton) which are accomodated in cartridges of relatively restricted dimensions and capable of working under pressure, a possibility which for technical reasons is not applicable to other filtration systems, such as for example those formed by so-called string filters, used industrially in this field. In this way, it should have been possible to obtain substantial improvements in terms both of space and of process speed.

It was, however, unexpectedly found that the membranes which would theoretically have been best, especially with regard to the characteristics of strength and of service life, such as for example those which are polysulphone-based, not only became obstructed within more or less brief periods of time depending upon the characteristics of the pharmaceutical preparation to be filtered, but in addition showed the property of impairing the actual composition of the formulation of the contrast medium. In fact, the membrane partially rejected the saline excipient (especially when said excipient is EDTA.Ca2Na), preferentially transmitting the non-ionic iodine-containing agent. This phenomenon, which was entirely unexpected and, according to the actual supplier of the membrane, unforeseeable for pharmaceutical solutions of this type, made it impossible to apply this technique for the desired purpose.

Nor could the performance of the membrane be restored by the frequent use of detergents, for example after each working cycle, as the aforementioned phenomenon was already manifested after the passage of a few hundred litres of solution. Nor did it prove possible to resolve the problem in an acceptable manner by changing the type of filtering material. Finally, complex experimentation led to the identification of a class of membranes, in essence those which are cellulose-based, which enabled the desired pyrogen retention to be obtained without impairing to a substantial extent the composition of the formulation. However, it was not possible to prevent said membrane from becoming obstructed in a short period of time.

The insertion of prefilters upstream of the ultrafiltration unit proved to be equally disappointing as, by reason of the particular characteristics of high concentration and viscosity of the solutions in question, in addition to the very fine microimpurities contained in these solutions, said prefilters lost their effectiveness by becoming obstructed prematurely under the pressure conditions necessary for obtaining acceptable prefiltration times. It was possible to obviate this defect only by arranging a series of prefilters connected in parallel, where said filters were connected to one another by a complex bypass system the function of which was to switch the solution to be depyrogenated from one prefilter to the next, without having on each occasion to interrupt the process in order to replace the prefiltering cartridge which had become obstructed. All this involved the construction of a plant which was complex and bulky and the management of which was sophisticated and costly. Furthermore, the final yield of the process proved in every case to be suboptimal by reason of the dead spaces due to the prefiltration system. To demonstrate the situation in a clearer fashion, a diagrammatic description of the plant is shown in FIG. 1.

As indicated therein, the solution to be depyrogenated is driven from the feed-tank A through the prefilter to the collection tank D under pressure conditions such as to ensure total flow rates of 1200/1500 and even more L/h, irrespective of the prefilter used (a substantially lower flow rate would not be acceptable in the general economics of the process, involving excessively long total filtration time).

These conditions of high pressure, especially with highly viscous solutions, cause the rapid obstructing of the prefilter, which would need to be replaced on a plurality of occasions for each working cycle. As a consequence, there would be an extension of the overall time, loss of product and the possibility of contamination.

The adoption of a series of prefilters (C1, C2, C3) connected in parallel and controlled by a bypass (B) which diverts from one filter to the next the solution arriving from A permits the completion of the working cycle in the times and under the working conditions which are desired, without having to interrupt the process.

Naturally, the disadvantageous aspects of this process are connected with the complexity of the prefiltering system, with the space necessary to accommodate the same and the high maintenance costs, bearing in mind that exhausted filters have to be removed and replaced by new ones. These problems assume ever greater importance the more substantial is the batch to be purified, as the number of cartridges to be used for each cycle is dependent both upon the working conditions (for example, the pressure applied and the temperature), and also upon the total volume of the solution to be treated.

On the other hand, the possible alternatives consisted of the adoption either of a very much larger and bulkier prefilter or of substantially lower pressure values, both parameters not being applicable to industrial processes involving batches of at least 800–1500 L of formulation.

The prefiltered solution is collected in a second tank D, from which it is subsequently taken off and pumped to the filtering unit E in accordance with the procedures which are normally employed in ultrafiltration. The depyrogenated filtrate ends up in a suitable collector where, before being packaged, it will be rehomogenized under agitation, while the residue, progressively enriched in pyrogens, is fed back to the tank D, being diluted, and then recycled to the filter E until such time as the entire process is completed.

It has now unexpectedly been found that it is possible to solve in an optimal fashion the above discussed problems by virtue of a process which can be carried out by means of a very simple filtration plant, of modest dimensions, which plant can be managed in an economical fashion and is capable of giving a high total yield both in terms of quality and in terms of quantity.

The process of the invention comprises the following steps:
prefiltration of said solutions by means of a microfiltering unit,
passing the solution deriving from the preceding step to the ultrafiltration unit, in which said ultrafiltration unit is equipped with tangential-ultrafiltration membranes having a porosity such as to deny passage to bacterial endotoxins and in which the retentate from said unit is directly recycled to the solution which emerges from the prefilter, while the permeate, complying with the limits set by the pharmacopoeia for the pyrogen content, is collected in a collector, where it is homogenized under agitation before packaging.

Figure 2:
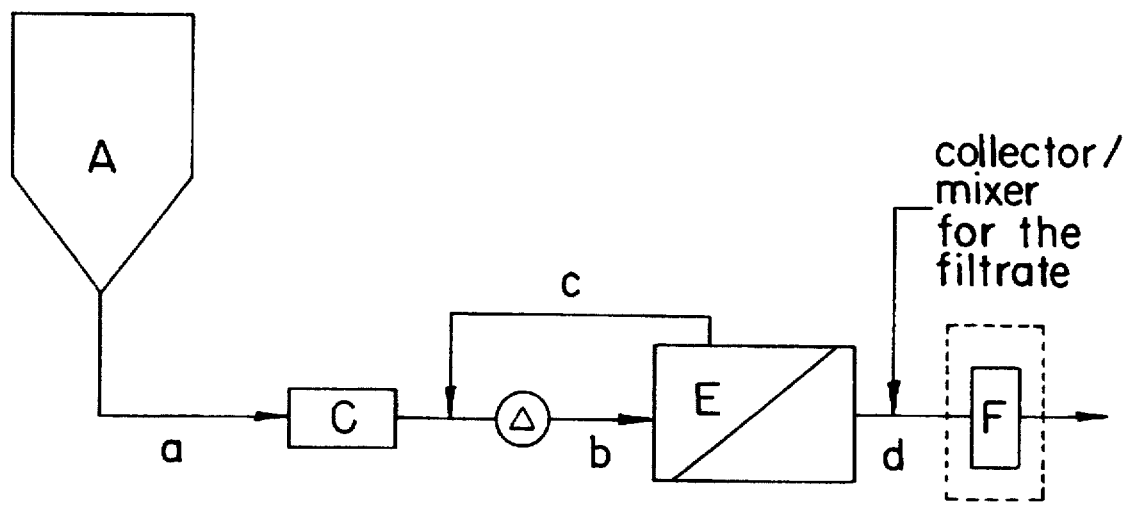
FIG. 2 illustrates the process according to the present invention.

The process of the invention may conveniently be carried out using a plant, diagrammatically illustrated in FIG. 2, which is extremely compact as it uses only a single prefiltration unit C, and unexpectedly does not require a tank for collecting the prefiltrate. The prefilter may take various forms, for example one or more filtering cartridges of decreasing porosity connected in series with one another. By way of example, a preferred configuration may comprise two filtering cartridges, of 1μ and 0.22μ respectively. Equally preferred is for example a prefilter constituted by a single composite filtering cartridge, that is to say one having decreasing porosity, with an average porosity of 0.5μ. In substance, the solution to be depyrogenated is driven through the prefilter C by virtue of a modest pressure applied from the exterior to the tank A (acceptable values range from 1 to 3 atm, preferably from 1.5 to 2.5 atm).

As it emerges from the prefilter, the solution is pumped directly to the ultrafiltration unit: the depyrogenated permeate is collected in a suitable collector provided with agitation and the retentate is recycled directly upstream of the pump which manages the ultrafiltration, to be admixed with the solution passing out from the prefilter. The ultrafiltering unit may be variously constituted: one of the preferred configurations may, for example, comprise a plurality of filtering modules (housings), in their turn comprising one or more filtering cartridges, said housings being capable of operating simultaneously or individually, depending upon the quantity of solution to be filtered. The membranes which are preferably used are those which are capable of preventing a substantial impairment of the composition of the formulation during the process (for example, permitting the preferential passage of one or more constituents as compared with the others) and having a porosity such as to prevent the passage of bacterial endotoxins.

From this point of view, cellulose-based membranes have proved to be particularly preferred, especially those of regenerated cellulose, with an average cut-off of 10,000 dalton. An absolutely non-limiting example of these is represented by spiral-wound cartridges of regenerated cellulose S10Y10$^{(R)}$ and/or S40Y10$^{(R)}$ (Amicon).

The transmembrane pressure applied to the ultrafiltration unit varies, depending upon the type of filtering cartridge employed and upon the characteristics of the solution to be filtered (by way of example, a very important factor is the concentration and thus the viscosity of said solution).

As a general rule, entirely acceptable results are obtained by applying transmembrane pressures which are variable between 1 and 5 atm. Naturally, when it is necessary to depyrogenate less viscous solutions, it will be possible to obtain high flow rates (and therefore shorter times) when applying a lower transmembrane pressure.

The flow rates which are obtainable may normally vary between 4 L/h per m$^2$ of filtering surface and 70 L/h·m$^2$, preferably between 6 and 55 L/h·m$^2$.

The operating temperature is another important parameter, and is dependent upon the thermal stability of the diagnostic formulation to be filtered and upon the limits imposed by the filtering material. In the case of cellulose-based membranes, particularly with those of regenerated cellulose, it is possible to operate at from 20° to 55° C., for example. Particularly preferred, in the case of highly concentrated and viscous solutions, is a temperature of approximately 50°–54° C., preferably 52° C.±2° C., while in the case of less viscous solutions it is preferred to operate at temperatures of approximately 30° C.

An absolutely non-limiting example is represented by the filtration of batches of 100–200 L of Iomeron$^{(R)}$ 150 (an injectable speciality containing the non-ionic iodine-containing contrast agent iomeprol in a concentration corresponding to a content of 150 mg/I per mL) in an AMICON SP150+52062 ultrafiltration unit equipped with S4010$^{(R)}$ ultrafiltering cartridges (Amicon) for a total filtering surface of approximately 11 m$^2$. Working at a temperature of 45° C.±5° C. and applying a transmembrane pressure which is variable from batch to batch from 1 to ~4 atm, flow rates were obtained which were within the range between approximately 12 and 45 L/h per m$^2$ with filtration times (for batches of 200 L) within the range between 0.4 and 1.5 h.

Another example of the invention may be represented by the depyrogenation of an industrial batch of 1,000 L of Iopamiro$^{(R)}$ 300 (an injectable speciality containing the non-ionic iodine-containing contrast agent iopamidol in a concentration corresponding to a content of 300 mg/I per mL) carried out in an Amicon SPM480 unit equipped with cartridges of regenerated cellulose for a total filtering surface of approximately 45 m$^2$, average cut-off of 10,000 dalton. Working at a temperature of 52° C.±2° C. and applying a transmembrane pressure of 3.5 atm, a flow rate of ~11 L/h per m$^2$ is obtained for a total filtration time of approximately 2 h.

The plant constructed proved to be surprisingly efficient, especially because, with the elimination of the tank D (typical of an ultrafiltration process: as a common practice, where there are no prefiltration problems, the residue is directly recycled, becoming diluted, to the feed tank, something which is obviously not possible in the present situation), the retentate c, becoming admixed directly with the flow arriving from the prefilter, causes an almost immediate increase in the concentration of toxins in the solution to be filtered. This fact should obviously impair the efficiency of the filtering unit.

However, the efficiency of the process proves to be optimal and the actual life of the cellulose filter proves to be surprisingly long, whereas its greater structural delicacy had initially greatly discouraged the continuous use thereof for the filtration of highly viscous solutions, such as for example X-ray diagnostic solutions, and especially at temperatures which are very close to the operating limits prescribed for said filter.

The fact that the process is a single-stage process eliminates the time wasted in collecting the prefiltrate in the tank D of FIG. 1. It further proves to be possible to operate at moderate operating pressures, with obvious benefits regarding the safety of the plant.

There is thus created a single-stage process (on the contrary the one illustrated in FIG. 1 is in essence a two-stage process) which is economical, is in full compliance with the most stringent regulatory standards, is highly efficient and is also entirely in line with the requirement to show care for the environment because it eliminates the need to use detergents to clean and restore the filtering surfaces (a simple step of sanitizing said surfaces, for example with soda, is sufficient). This gives a drastic improvement from the point of view of the impact on the environment. Furthermore, this also removes the need to eliminate every residual trace of detergent and the need then to analytically certify its absence. All this brings clear benefits in terms of costs and quality of the finished product as well.

If required, it is also possible to insert at the outlet, preferably downstream of the collector/mixer of the filtrate (not indicated in FIG. 2), a further sterilizing filter of 0.2μ or even less (F, indicated in the outlined zone of FIG. 2), thus obtaining a final solution which is homogeneous and entirely sterile, ready to be made up.

The flow rate remains substantially constant throughout the entire duration of the process. In this way, it remains possible to treat preparations up to 800–1,500 L in modest times (1.5–5 h) with yields of up to 97–98%, obtaining a product which is in full compliance with the most stringent pharmacopoeia limits.

The plant of FIG. 2 has proved to be particularly useful for the depyrogenation of diagnostic injectable pharmaceutical formulations. Radio-opaque diagnostic formulations comprising as contrast agent a non-ionic iodine-containing compound or a mixture of iodine-containing compounds, either or monomeric or of dimeric type, have proved to be particularly preferred.

Absolutely non-limiting examples of iodine-containing radio-opaque contrast agents, injectable formulations of which can be depyrogenated by means of the process and the plant of the invention, may be selected from among the following monomeric and dimeric compounds and mixtures thereof: iopamidol, iomeprol, iohexol, ioversol, iopentol, iopromide, ioxilan, iotriside, iobitridol, iodixanol, iofratol, iotrolan, iodecimol, iopirol, iopiperidol.

Equal preference has proved to be ascribable to the injectable formulations of contrast agents for NMR imaging, usually comprising, as contrastographic ingredients, chelates of paramagnetic metal ions (such as for example Gd$^{3+}$, Mn$^{2+}$, Fe$^{3+}$, Eu$^{3+}$, Dy$^{3+}$ etc.) with chelating agents of various types (such as for example linear or cyclic polycarboxylic polyamino acids, and derivatives or salts thereof, polyaminophosphonic or polyaminophosphinic acids and derivatives thereof etc.).

Absolutely non-limiting examples of contrast agents of this type may be selected from among the following: chelate of Gd$^{3+}$ with diethylenetriamine pentaacetic acid (Gd-DTPA), chelate of Gd$^{3+}$ with 1,4,7,10-tetraazacyclododecan-1,4,7,10-tetraacetic acid (Gd-DOTA), chelate of Gd$^{3+}$ with [10-(2-hydroxypropyl)-1,4,7,10-tetraazacyclodecan-1,4,7-triacetic acid (Gd-HPDO3A), chelate of Gd$^{3+}$ with 4-carboxy-5,8,11-tris(carboxymethyl)-1-phenyl-2-oxa-5,8,11-triazatride-can-13-oic acid (Gd-BOPTA), chelate of Gd$^{3+}$ with N-[2-|bis(carboxymethyl) amino]-3-(4-ethoxyphenyl)propyl]-N-(2-[bis (carboxymethyl)amino]ethylglycine (Gd-EOB-DTPA), chelate of Gd$^{3+}$ with N,N-bis[2-[(carboxymethyl)| (methylcarbamoyl)methyl]amino]ethyl]-glycine (Gd-DTPABMA), chelate of Gd$^{3+}$ with (α,α',α'',α''')-tetramethyl-1,4,7,10-tetraazocyclododecan-1,4,7,10-tetraacetic acid (Gd-DOTMA), chelate of Mn$^{2+}$ with N,N'-bis(pyrodoxal-5-phosphate)ethylene-diamine-N,N'-diacetic acid (Mn-DPDP) and salts or derivatives thereof, such as for example those of amide or ester type.

We claim:

1. A process for the depyrogenation of an injectable pharmaceutical solution of a contrast agent comprising the following steps:

a) prefiltering said solution by means of a microfiltering unit to obtain a second solution;

b) passing said second solution from step a) to an ultrafiltration unit, said ultrafiltration unit consisting of at least one filtration module, said module being equipped with tangential-ultrafiltration membranes having an average cut-off of 10,000 dalton, said module being capable of operating simultaneously or individually, wherein said tangential-ultrafiltration membranes are cellulose-based and have a porosity such as to deny passage to bacterial endotoxins whereby a permeate and a retentate are obtained, the retentate from said unit is directly recycled to said second solution which emerges from step a), while the permeate, complying with the limits set by the pharmacopoeia for the pyrogen content, is collected in a collector, where it is homogenized under agitation before being packaged.

2. The process according to claim 1 wherein said membranes are of regenerated cellulose.

3. The process according to claim 1 wherein said microfiltering unit is constituted by a single composite filtering cartridge having decreased porosity of average porosity 0.5μ.

4. A plant for depyrogenating, by means of tangential-ultrafiltration an injectable pharmaceutical solution of a contrast agent which consists essentially of a tank (A), a single prefiltration unit (C), said solution being fed from said tank (A) to said prefiltration unit (C), said prefiltration unit (C) comprising one or more filtering cartridges of decreasing porosity connected in series with each other, an ultrafiltration unit (E) pumping means for pumping said solution from said prefiltration unit (C) to said ultrafiltration unit (E), where a depyrogenated permeate is separated from the retentate, a collector, said permeate is collected in said collector, means for recycling said retentate by mixing it with said solution upstream of said pumping means, and the plant comprises a sterilizing filter (F) located downstream of said collector.

5. A plant for depyrogenating, by means of tangential-ultrafiltration an injectable pharmaceutical solution of a contrast agent which consists essentially of a tank (A), a single prefiltration unit (C), said solution being fed from said tank (A) to said prefiltration unit (C), said prefiltration unit (C) comprising a single composite filtering cartridge having decreasing porosity, an ultrafiltration unit (E) pumping means for pumping said solution from said prefiltration unit (C) to said ultrafiltration unit (E), where a depyrogenated permeate is separated from the retentate, a collector, said permeate is collected in said collector, means for recycling said retentate by mixing it with said solution upstream of said pumping means, and the plant comprises a sterilizing filter (F) located downstream of said collector.

* * * * *